United States Patent [19]
Fortune

[11] 3,980,218
[45] Sept. 14, 1976

[54] VACUUM DESOLDERING SYSTEM

[76] Inventor: William S. Fortune, 14250 Dearborn St., Panorama City, Calif. 91202

[22] Filed: Aug. 4, 1975

[21] Appl. No.: 601,277

[52] U.S. Cl. .................................. 228/20; 15/395; 137/625.68; 137/627.5; 228/57
[51] Int. Cl.² .......................................... B23K 3/00
[58] Field of Search ............... 228/20, 57; 219/230; 137/625.68, 625.69, 627.5; 15/395

[56] References Cited
UNITED STATES PATENTS

| | | | |
|---|---|---|---|
| 3,549,078 | 12/1970 | Fortune | 228/20 |
| 3,563,273 | 2/1971 | Mills | 137/625.69 |
| 3,842,240 | 10/1974 | Wakita et al. | 228/20 X |

*Primary Examiner*—Al Lawrence Smith
*Assistant Examiner*—K. J. Ramsey
*Attorney, Agent, or Firm*—Daniel T. Anderson

[57] ABSTRACT

A hand held, vacuum operated desoldering tool and a holder fixture therefor is disclosed in which the desoldering tool has a tubular, barrel body with a nozzle tip forward end and a vacuum line attachment fitting at its opposite, rear end. A trigger is disposed in a trigger housing formed contiguously to the rear end for connecting the vacuum line to the interior of the barrel body and forward tip end of the tool. Thus when the trigger is actuated by the fingertip of the operator, the body is evacuated and an impulse of air is drawn thereinto through the forward nozzle tip of the tool for a desoldering operation. A baffle and filter are disposed within the tubular body to prevent solder and other particles from entering the trigger mechanism and the vacuum supply line.

Another component of the combination disclosed is a tool holder and power tip cleaner for the desoldering tool. The tool holder includes a short, large diameter cylindrical body which carries a power piston. The piston, in turn, carries a centrally axially disposed tip cleaning rod. When the tip end of the desoldering tool is nested within the tool holder and its trigger actuated, the power piston is drawn toward the desoldering tool with the tip cleaning rod pushing through the nozzle in a bore cleaning action. When the trigger is released, atmospheric pressure and a piston return spring force the power piston and its cleaning rod to withdraw away from the desoldering tool nozzle.

7 Claims, 4 Drawing Figures

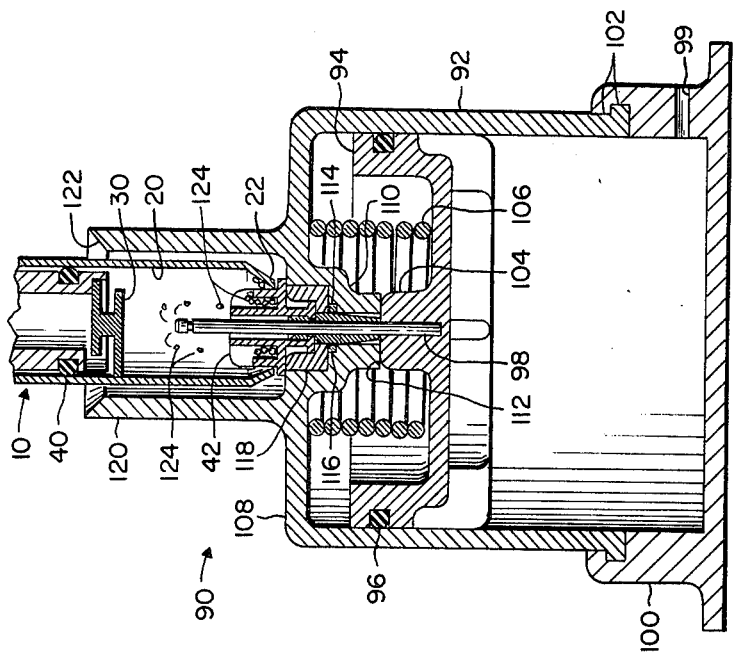
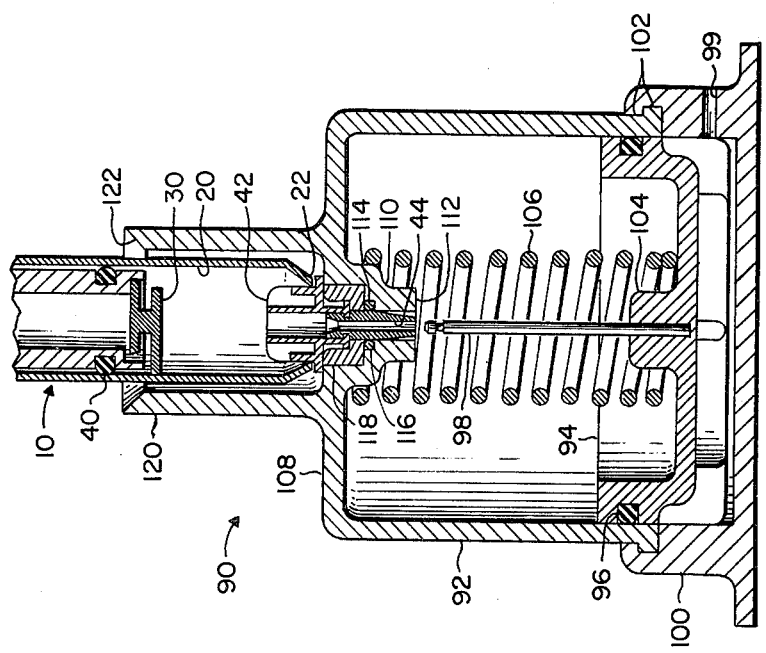

VACUUM DESOLDERING SYSTEM

BACKGROUND OF INVENTION

1. Field of the Invention

The invention relates generally to removing or lifting or drawing away, by air suction technique, small quantities of particulate, liquid, or molten matter and particularly to apparatus improvements in hand held, vacuum cleaning devices. The present invention finds particularly useful application in the field of soldering, desoldering, and rewiring in electronic laboratories, maintenance shops, factories, or hobbyists' benches; and although, in the cause of clarity and brevity, much of the following discussion and description of examples of the invention are directed theretoward, it is expressly to be understood that the advantages of the invention are equally well manifest in other fields wherever and whenever substances are to be removed or cleaned from an object such, for further example, in medical or dental fields, as in removal of foreign objects or unwanted substances from portions of the body including the eye, ear, nose, throat, or open wound or the like.

2. Background of the Invention

In the electrical arts as mentioned, it is often desired to desolder an electrical connection such as, for example, a wire wrapped terminal, a wire to circuit board eyelet, or the like. The removal from the connection, of the molten solder without dropping or spattering it onto other portions of the equipment is generally essential. Blowing or shaking the molten metal away is therefor not an acceptable practice; and, in combination with its high mass density, the high surface tension associated with the solder makes its removal particularly difficult. Furthermore, the problem is aggravated by the requirement that the solder be removed quickly and without application of cooling means before the mechanical connection such as a wirewrapped terminal may be taken apart.

Various non-portable central vacuum systems and highly portable and efficient hand held vacuum stroke tools have advanced the state of the art and have solved certain aspects of the desoldering problems outlined; however, the former have heretofore suffered from disadvantages of cost, complexity, lack of versatility, and non-portability while the latter suffer from some disadvantages, to a lesser extent, of cost and complexity, and, in some applications, undesirable recoil due to the flyback action of the piston cocking shaft-knob assembly during the vacuum stroke, the recoil causing a deflection of the solder inlet tip into the location of the molten solder.

This recoil caused displacement is particularly intolerable in medical applications such as in removing foreign matter from a patient's eye.

Another disadvantage of central vacuum systems is the difficulty of maintaining the tip inlet nozzle clear of interferring foreign substance such as solidified solder.

It is, accordingly, an object of the present invention to provide improved vacuum operated, cleaning apparatus which is not subject to these and other disadvantages and limitations of the prior art.

It is another object to provide such apparatus which, while providing consistently a high amplitude of impulse air flow, has no flyback portion and no deflection of the tool during its vacuum operated cleansing action.

It is another object to provide such apparatus which is exceedingly low in cost, is miniature and simple, and is rugged, and reliable in its structure and performance.

It is another object to provide such apparatus which may readily be molded of low cost, recyclable plastic materials.

It is another object to provide such apparatus, the outer body of which may be clear plastic to permit continuous inspection of its condition and performance.

It is another object to provide such apparatus the nozzle tip of which is self-cleaning.

It is another object to provide such apparatus having readily removable and replaceable tip means particularly in medical uses for assuring the effective sterility of the implement.

SUMMARY OF INVENTION

Briefly, these and other objects are achieved in accordance with the structural aspects of an example of the invention in which a vacuum operated desoldering tool and holder-cleaner combination is provided in which the desoldering tool includes a tubular barrel having a forward end for holding a removable nozzle tip member. The central portion of the barrel houses a baffle and filter assembly for retaining foreign materials which have entered through the nozzle tip. The rear end portion of the barrel includes trigger housing means and a finger actuated trigger which selectively connects a flexible external vacuum line to the central portion of the barrel causing a rapid flow of air thereinto through the nozzle tip.

In this example, the invention also includes a tool holder and power cleaning fixture for the bore of the nozzle tip. The power cleaning fixture comprises a vertical axis, large diameter, short cylindrical body portion housing a piston which is retained normally at the bottom of the cylinder by a compression, return spring. The piston carries a tip cleaning shaft extending centrally upwardly. The tool holder comprises an upwardly open, short cylindrical body for retaining the tool, tip end down, in a vertical orientation. The tool holder body is mounted coaxially upon the top of the power cleaning fixture body and has a central opening which communicates with the interior of the upper portion of the latter. An o-ring seal is provided about the inner periphery of this opening whereby when the tool is retained in the tool holder, the interior of the tool barrel is in air flow communication with the otherwise closed, upper portion of the tool holder body; and these intercommunicating portions are essentially sealed from the external environment. Accordingly, then, when the tool is thus emplaced within the tool holder and at the same time its trigger is actuated to evacuate the barrel body of the tool, the power piston of the cleaning fixture is drawn upwardly forcing its tip cleaning rod through the nozzle tip thereby ejecting any foreign substances held therein into the interior of the barrel body of the tool.

A bleeding path is provided from the atmosphere through the trigger mechanism whereby when the latter is released, the tool is isolated from the vacuum line and atmospheric pressure is impressed through the nozzle tip into the upper region of the tool holder body. The return spring then forces the power cleaner piston to travel back to its lower, at rest position. To assure this flow of air to release the power piston, a relief vent along the length of the cleaning rod is provided.

Further details of these and other novel features and their operation and cooperation as well as additional objects and advantages of the invention will become apparent and be best understood from a consideration of the following description taken in connection with the accompanying drawings which are provided by way of illustrative example only.

BRIEF DESCRIPTION OF THE DRAWING

FIG. 3 is a sectional view illustrating the tool holder, tip power cleaner portion of this example of the invention with the tool retained in a storage mode therein; and FIG. 4 is a similar view illustating the power cleaning stroke of the tool holder.

DETAILED DESCRIPTION OF PREFERRED EMBODIMENT

Figure 1:
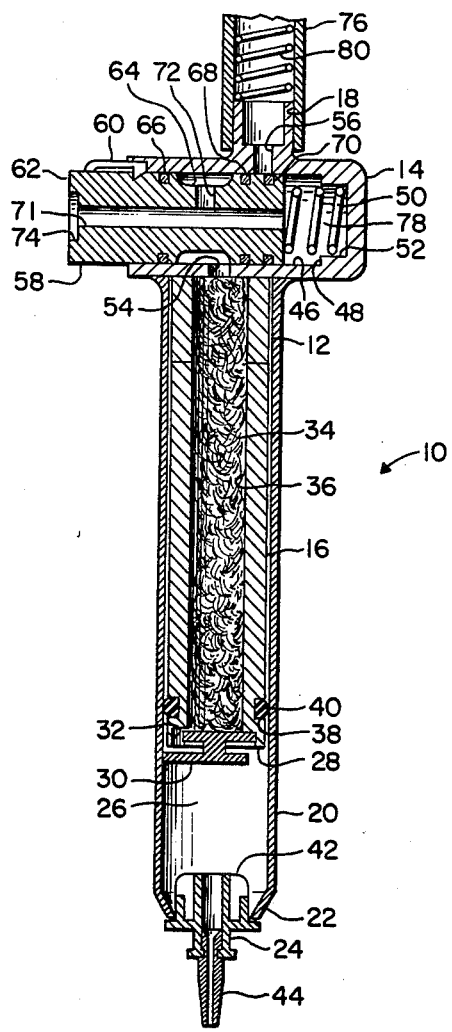
FIG. 1 is an elevational view, shown partially in longitudinal section of the vacuum tool portion of a vacuum desoldering system constructed in accordance with the principles of the present invention, the tool being illustrated in an at rest, untriggered configuration.

With specific reference now to the figures in detail, it is stressed that the particulars shown are by way of example and for purposes of illustrative discussion only and are presented in the cause of providing what is believed to be the most useful and readily understood description of the principles and structural concepts of the invention. In this regard, no attempt is made to show structural details of the apparatus in more detail than is necessary for a fundamental understanding of the invention. The description taken with the drawing will make it apparent to those skilled in the mechanical arts how the several forms of the invention may be embodied in practice. specifically, the detailed showing is not to be taken as a limitation upon the scope of the invention which is defined by the appended claims forming, along with the drawings, a part of this specification.

In FIG. 1, the example illustrated of the vacuum operated tool 10 includes a molded body 12 having a trigger housing portion 14, a cylindrical, inner barrel portion 16, and a vacuum line connector 18. An outer cylindrical barrel 20 is provided which has an inner diameter approximately equal to the outer diameter of the inner barrel portion 16 and a length somewhat greater than that of the barrel portion 16. The forward end 22 of the outer barrel 20 has a reduced diameter for retaining a removable tip assembly 24. A reservoir space 26 is formed within the forward portion of the outer barrel 20 between its end 22 and the forward end 28 of the inner barrel portion 16 which includes a baffle 30 retaining lip 32. The baffle 30, in addition to blocking foreign particles while not impeding air flow, retains a course filter 34, such as, for example, a quantity of metallic "wool", within the main bore 36 of the barrel portion 16.

An annular retaining groove 38 may be provided about the outer surface of the barrel portion 16 to retain an o-ring 40 which provides a seal for the two telescopically joined bodies and adds, in addition, a desirably stabilizing magnitude of friction therebetween. For disassembly, in order to remove foreign materials from the reservoir 26 as well as to remove, clean, or replace the filter 34, the outer barrel 20 is simply pulled forwardly over the inner barrel portion 16 away from the rear, trigger housing end of the body 12 until the two telescopically related barrel portions are totally parted. The filter and baffle may then be cleaned; and the reservoir areas may be cleaned and lightly oiled to minimize the sticking thereto of molten bits of solder in future desoldering operations. For ease in inspection of the reservoir area and to determine its need for cleaning, the outer barrel 20 may, desirably, be molded of a transparent plastic.

Access to the reservoir 26 may also be achieved by removing the frictionally retained tip assembly 24. The assembly 24 may include a molded base portion 42 and a tip element 44 machined from a heat resistant material such as Teflon or the like.

The trigger housing portion 14 of the body 12 is provided with a main bore 46 disposed transversely to the axis of the barrel members and terminates in a trigger stopping shoulder 48. A smaller diameter, trigger return spring 50 retaining recess bore 52 may continue to a greater depth as shown. An inlet port 54 connects the bore 46 to the main bore 36 of the barrel portion 16; and an outlet port 56 connects the bore 46 to the vacuum line connector 18.

A trigger spool 58 is retained axially slidably within the bore 46 by a retaining clip 60. The trigger spool 58 includes a finger actuating end 62, projecting accessibly from the trigger housing portion 14, and a reduced diameter mid-portion 64 bounded by a pair of 0-ring seals 66, 68. The seal 68 is also one of a pair of seals 68, 70 which are axially spaced to either side of the outlet port 56 so that, normally, that port is isolated and effectively closed. When, however, the trigger spool 58 is moved axially against its return spring 50 so that the o-ring seal 68 is disposed on the opposite side of the outlet port 56, the axial spacing of the seals 66, 68 is sufficient to interconnect the inlet and outlet ports 54, 56 and consequently evacuate the internal regions of the barrel bodies 16, 20 and create a current of air through the tip element 44.

The trigger spool 58 is provided with a central, pilot bore 71 which extends through the entire length of the spool. In addition, the reduced diameter portion 64 of the spool is connected to the pilot bore 71 by a transverse bore 72.

In operation, when the operator's finger tip, not shown, is placed over the end 62 of the trigger spool, the end 74 of the pilot bore 72 is closed by the impressed finger tip. In turn, when the seal 68 passes beyond the first edge of the outlet port 56, the reduced pressure of the vacuum line 76 is applied, through the transverse bore 72 and the central, pilot bore 70 to the enclosed space 78 at the bottom of the trigger housing bores 46, 52. Evacuating the space 78 provides a helpful power boost to the remaining action of the trigger operation. The boost provides a more rapid trigger action and therefore a sharper impulse of working air through the nozzle tip 44. In addition, for so long as the operator's finger tip remains in a sealing relation over the opening 74, no effort is required by the operator against the spring 50 since force due to atmospheric pressure retains the trigger fully depressed. When, however, the operator's finger tip is removed, atmospheric pressure is applied to the region 78, and the spring 50 returns the trigger to its normal, closed position, as shown. Another function of the pilot bores 71, 72 is to permit, when the trigger is closed, the impression of atmospheric pressure through the inlet port 54 into the tool barrel for purposes discussed below.

The vacuum supply line 76 may be a thin-walled flexible tube of rubber, neoprene, or other appropriate material. To control the impulse of air flow through the nozzle tip when the trigger is actuated, a metal, supporting helix 80 may be inserted, as shown, along the full length of the line 76. The helix prevents the collapse of the line 76 and assures, instantly, a full flow of air when the trigger is actuated.

Figure 2:
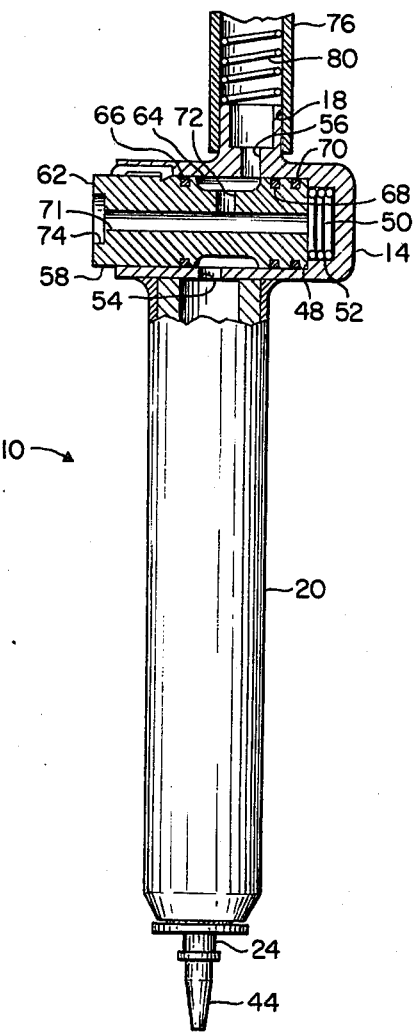
FIG. 2 is a similar view shown fully in section and in a triggered, action configuration.

Referring to FIG. 2, the structure illustrated and described in connection with FIG. 1 is shown with the trigger spool 58 actuated, i.e., fully depressed, against the compression, trigger return spring 50. As discussed above, this disposition of the trigger spool is stable and requires no application of force from the operator's finger tip except to keep the opening 74 of the vent bore 71 closed against the atmosphere; and this action tends to be stable because of the reduced pressure maintained within the bore 71.

When, however, the operator's finger tip is removed, atmospheric pressure is impressed against the inner surface of the trigger spool in the region 78, and the spool is abruptly returned to its normal, closed disposition shown in FIG. 1.

In FIG. 3, the tool 10 is shown retained or held in a storage mode by the tool holder assembly 90. The holder, in this example, comprises a main power cylinder body 92 containing a power piston 94 with a peripheral piston sealing o-ring 96 and carrying a tip bore cleaning rod 98 extending axially upwardly from the center of the piston 94. The diameter of the rod 98 may be approximately equal to that of the bore of the tip nozzle 44. Additionally, one side of the rod may be flat to provide a vent for air passage while the rod is in the bore. A relief vent for that portion of the cylinder in back of or below the piston 94 is provided by a port 99 communicating through the wall of the cylinder body to the atmosphere. The bottom of the cylinder body 92 is secured to a base member 100 by a bayonet twist-lock mechanism 102 to permit disassembly for maintenance and lubrication. An increased thickness portion 104 contiguous to the center of the piston 94 provides a reinforced supporting structure for the cleaning rod and a retaining shoulder for a piston return spring 106 disposed in compression along the length of the power cylinder between the piston 94 and the upper end 108 which esentially closes the top of the power cylinder body 92.

An increased thickness portion 110 of the end 108 provides a nozzle tip holder 112 which includes an o-ring seal 114 secured between a retaining shoulder 116 and a retaining sleeve 118. A tool holder well 120 is molded integrally with the power cylinder body 92 and is disposed centrally, in line with the tip holder 112. The upper opening 122 of the holder well 120 may be tapered inwardly to provide a funneling action helpful to the operator when the tool is placed in the holder assembly. The retaining sleeve 118 may be similarly shaped to provide an additional funneling action for the nozzle tip as it enters the tip holder 112.

Again, it should be understood that the configuration of the structure shown in FIG. 3 is that resulting from the tool 10 being disposed in the holder assembly in a storage mode; and, in particular, the trigger is not actuated, the interior of the tool is not evacuated, and atmospheric pressure is impressed equally upon both faces (top and bottom) of the power piston 94.

In FIG. 4, on the other hand, the system is illustrated in its configuration when the trigger has been actuated, the interior of the tool has been evacuated, the upper volume of the power cylinder has been evacuated by means of air flow therefrom through the nozzle tip 44, and atmospheric pressure applied against the bottom of the piston 94 through the vent port 98 has caused the power piston to travel upwardly forcing the tip cleaing rod 98 to pass through the clogged bore of the tip 44 and eject the foreign material 124 into the resevoir 26.

When the trigger is again released, air at atmospheric pressure is vented through the venting bores 71, 72 of the trigger spool 58, (see FIG. 1) through the interior of the tool 10 and the nozzle 44, along the side of the cleaning rod 98, to equalize the air pressures acting on the power piston 94 so that its return spring 106 forces it to return to its normal position shown in FIG. 3.

It may be noted that during this return nozzle of the power piston, the operator is well able to feel or sense the magnitude of air flow into the venting bore past his finger tip and judge therefrom whether the tip bore has been satisfactorily cleaned of foreign substance. If the venting flow is sensed to be too small, a second power cleaning stroke may be achieved to assure that the bore is fully cleared.

There has thus been disclosed and described an example of a vacuum desoldering system which achieves the objects and exhibits the advantages set forth hereinabove.

What is claimed is:

1. Hand held and hand operated vacuum desoldering apparatus of the character to be connected to and driven by an external vacuum source, the apparatus comprising:
    a tubular body member having a forward, end and a rearward, end and a barrel portion interposed therebetween;
    tip means removably carried by said body member contiguously to its said forward end and having a central bore provided therethrough for drawing molten solder into said barrel portion of said tubular body member; connector means carried by said body member for interconnecting said body member and the external vacuum source;
    trigger valve means carried by said body member contiguously to said rearward end for time selectively interconnecting said connector means with said barrel portion of said tubular body member, said trigger valve means including
    trigger housing element affixed to said tubular body member,
    air inlet duct means interconnecting said housing element with said barrel portion,
    air outlet duct means interconnecting said housing element with said connector means,
    finger operable, movable valve body means carried by said housing element for selectively and alternatively isolating said air outlet means and interconnecting it with said air inlet means, and
    filter means disposed in said barrel portion for blocking foreign substance from traversing said air inlet means,
    said trigger housing element further comprising a valve bore having a predetermined axis defining a direction of operating motion of said finger operable valve body means axially movably disposed therewithin, said inlet and outlet duct means being spaced apart along said axis by a distance a, said movable valve body means comprising,
  valve spool element having a normal, outlet duct closed, axial disposition and a triggered, outlet-inlet ducts interconnected, axial disposition,
  first and second sealing rings carried by said spool element and spaced by an axial distance b which is greater than a, said first sealing ring being axial disposed to the side of said inlet duct opposite from said outlet duct irrespective of whether said spool element is in its said normal or triggered disposition, said second sealing ring being disposed on the side of said outlet duct toward said inlet duct when said spool element is in its said normal disposition, thereby to isolate said ducts, and being disposed on the side of said outlet duct opposite from said inlet duct when said spool element is in its said triggered disposition, and said spool element being formed to provide interconnection means between said first and second sealing rings whereby said inlet and outlet ports are interconnected when said spool element is in its said triggered disposition, and third sealing ring carried by an inserted end of said spool element and disposed axially to the side of said outlet duct away from said inlet duct irrespective of whether said spool element is in its normal or triggered disposition,
said valve bore of said trigger housing element being formed to provide a trigger servo booster chamber between said inserted end of said spool element and said trigger housing element, and said spool element being formed to provide a first vent duct between its said inserted end, said booster chamber, and said interconnection means of said spool element between said first and second sealing rings.

2. The invention as set forth in claim 1 in which the end of said spool element opposite from its said inserted end is exposed for application of actuating force by an operator's finger tip and which includes a finger tip application region thereof, and in which said spool element is further formed to provide a second vent duct interconnecting said finger tip application region and said first vent duct.

3. The invention as set forth in claim 2 which further includes tool storage and power tip cleaning apparatus comprising:
  a hollow cylinder body having a base end and an opposite, top end and being of the character to rest on its said base end with its axis substantially vertical;
  a tool supporting well coaxial with said cylinder body and disposed on said top end thereof and being of the character to receive and retain in a storage mode said tubular body member when its said forward end and tip means are disposed therein in a vertical configuration essentially coaxial with said cylinder body and tool supporting well;
  a central opening formed between the bottom of said supporting well and the upper interior of said hollow cylinder body, said central opening being of the character to receive the tip portion of said tip means thereby to provide air flow communication between said hollow cylinder body and said barrel portion of said tubular body member; and
  sealing ring means disposed within said central opening for engaging the exterior of said tip portion and effectively sealing said barrel portion and hollow cylinder body from their external environment.

4. The invention as set forth in claim 3 which further includes a tip cleaning power piston disposed within and in a sliding seal relation with the internal cylindrical wall of said hollow cylinder body and being adapted to move axially up and down therein in response to the relative air pressures of said barrel portion of said tubular body portion and the external atmosphere, the hollow cylinder body including venting means disposed contiguously to its base end for applying atmospheric pressure to the lower side of said piston; and which further includes a tip cleaning rod means carried centrally by said piston and extending upwardly coaxially with said central opening and said tip portion for entering said tip portion and cleaning it when said piston is moved vertically upwardly.

5. The invention as set forth in claim 1 which further includes tool storage and power tip cleaning apparatus comprising:
  a hollow cylinder body having a base end and an opposite, top end and being of the character to rest on its said base end with its axis substantially vertical;
  a tool supporting well coaxial with said cylinder body and disposed on said top end thereof and being of the character to receive and retain in a storage mode said tubular body member when its said forward end and tip means are disposed therein in a vertical configuration essentially coaxial with said cylinder body and tool supporting well;
  a central opening formed between the bottom of said supporting well and the upper interior of said hollow cylinder body, said cetral opening being of the character to receive the tip portion of said tip means thereby to provide air flow communication between said hollow cylinder body and said barrel portion of said tubular body member; and
  sealing ring means disposed within said central opening for engaging the exterior of said tip portion and effectively sealing said barrel portion and hollow cylinder body from their external environment 6. The invention as set forth in claim 5 which further includes a tip cleaning power piston disposed within and in a sliding seal relation with the internal cylindrical wall of said hollow cylinder body and being adapted to move axially up and down therein in response to the relative air pressures of said barrel portion of said tubular body portion and the external atmosphere, the hollow cylinder body including venting means disposed contiguously to its base end for applying atmospheric pressure to the lower side of said piston; and which further includes a tip cleaning rod means carried centrally by said piston and extending upwardly coaxially with said central opening and said tip portion for entering said tip portion and cleaning it when said piston is moved vertically upwardly.

7. The invention as set forth in claim 6 which further includes a power piston return spring disposed within said hollow cylinder body and connected between said hollow cylinder body and said power piston to return it vertically downwardly when atmospheric pressure is applied to both its surfaces.

* * * * *